(12) United States Patent
Popot et al.

(10) Patent No.: US 6,492,501 B1
(45) Date of Patent: Dec. 10, 2002

(54) WATER SOLUBLE ACRYLIC MEMBRANE-POLYMER PROTEIN AMPHIPHILIC COMPLEX AND APPLICATION TO DIAGNOSIS METHODS

(76) Inventors: Jean-Luc Popot, 102 rue Léon Maurice Nordmann, 75013 Paris (FR); Christophe Tribet, Résidence du Parc, Bâtiment les Hêtres, 91700 Villiers-sur-Orge (FR); Roland Audebert, deceased, late of Saint Leu la Forêt (FR), by Françoise Audebert, Vincent Audebert, Agnès Audebert, Marc Audebert, executors ( * ) Notice: Subject to any disclaimer, the term of this patent is extended or adjusted under 35 U.S.C. 154(b) by 0 days.

(21) Appl. No.: 09/331,036
(22) PCT Filed: Dec. 16, 1996
(86) PCT No.: PCT/FR96/02009
§ 371 (c)(1),
(2), (4) Date: Nov. 5, 1999
(87) PCT Pub. No.: WO98/27434
PCT Pub. Date: Jun. 25, 1998

(51) Int. Cl.$^7$ ............... C07K 17/08; G01N 33/545; G01N 33/566
(52) U.S. Cl. ............ 530/402; 436/531; 530/815
(58) Field of Search ............ 436/531; 530/815, 530/402

(56) References Cited

U.S. PATENT DOCUMENTS

| 4,828,710 A | * | 5/1989 | Itoh et al. | |
|---|---|---|---|---|
| 5,223,411 A | | 6/1993 | Pulsquellec et al. | 435/71.2 |
| 6,172,262 B1 | * | 1/2001 | McQuade | |

FOREIGN PATENT DOCUMENTS

| EP | 0291389 | 11/1988 |
|---|---|---|
| EP | 0363106 | 4/1990 |
| WO | 9704796 | 2/1997 |

OTHER PUBLICATIONS

Petit, F., et al. "Interactions of Hydrophobically Modified Poly(Sodium Acrylate) with Globular Proteins." Colloid Polym. Sci, vol. 273, No. 8 (1995) pp 777–781.

Popot J–L, et al. "On The Microassembly of Integral Membrane Proteins". Annu. Rev. Biophys. Biophys. Chem., 19, (1990) pp 369–403.

Tribet,C.,et al. "Amphipols: Polymers that keep membrane proteins soluble in aqueous solutions" Proc. Natl. Acad. Sci. USA, vol. 93, No. 26, (1996), pp. 15047–15050.

* cited by examiner

*Primary Examiner*—Mary E. Ceperley
(74) *Attorney, Agent, or Firm*—Ladas & Parry

(57) ABSTRACT

The invention concerns a water soluble vinyl membrane-polymer protein amphiphilic complex, characterised in that said vinyl polymer corresponds to formula (I) in which: $R_1$ is a group: $COO^{\ominus} M^+$ $M^+$ being an alkaline cation, $COOR_7$, $R_7$ being a sugar radical; polyoxyalkylene, polyoxyethylene; N-pyrrolidonyl; phenyl sulphonate; $CONR_8R_9$, $R_8$ and $R_9$ identical or different being hydrogen atom, a sugar radical, polyoxyalkylene, in particular polyoxyethylene, a zwitterion radical; $R_4$, $R_5$, $R_6$ identical or different are hydrogen atom, or methyl radical; $R_2$ is a $COOR_{12}$ or $CONR_{13}R_{14}$ radical, $R_{12}$ being a linear or branched alkyl or alkylene radical; $R_{13}$, $R_{14}$ identical or different have one of the meanings of $R_{12}$, and moreover one of the two can correspond to hydrogen atom; $R_3$ is a $COOR_{15}$ or $CONR_{16}R_{17}$ radical; $R_{15}$ being a ($C_1$–$C_5$) alkyl radical; $R_{16}$, $R_{17}$ having one if the meanings of $R_{15}$ and moreover one of the two can correspond to hydrogen atom; x, y, z correspond to the respective percentages of units. The complex is applicable for producing reagent and diagnosis kits.

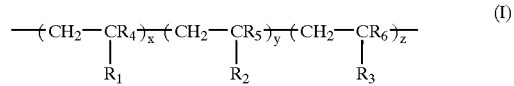

(I)

18 Claims, 1 Drawing Sheet

Figure 1:
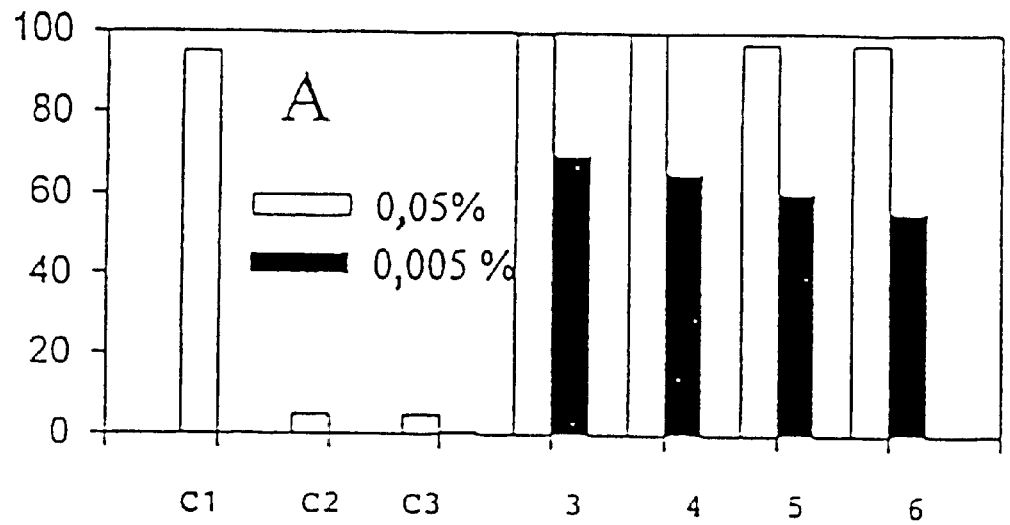

WATER SOLUBLE ACRYLIC MEMBRANE-POLYMER PROTEIN AMPHIPHILIC COMPLEX AND APPLICATION TO DIAGNOSIS METHODS

This is the US National Stagk Application of PCT/FR96/02009 filed Dec. 16, 1996.

The invention relates to novel membrane protein-vinyl polymer of amphiphilic nature water-soluble complexes, to a process for preparing these complexes and to the application of these complexes to diagnostic or analytical methods.

Integral membrane proteins, which are a specific class of proteins, are inserted in vivo into biological membranes and cross the lipid bilayer thereof. The surface of these proteins which naturally comes into contact with the membranes (transmembrane region) is particularly hydrophobic.

Membrane proteins ensure essential biological functions, in particular as regards the exchange of information or of molecules between the various cell compartments and between the cell and its environment. In this respect, they are of major value in the medical field. They represent, for example, preferred targets for medicinal molecules. They are also involved in many human diseases, some of which (for example multiple sclerosis or myasthenia gravis) have an autoimmune component manifested by the presence in the serum of autoantibodies directed against membrane proteins. Manipulation of membrane proteins in aqueous solution is usually a prerequisite which is essential to their purification and to their structural and functional study. It requires avoidance of the spontaneous aggregation of the hydrophobic domains and maintenance of a relatively nonpolar environment around the transmembrane regions.

The standard preparations of such proteins in the water-soluble state contain micellar concentrations of surfactants. The success of the process is based on the high affinity of the transmembrane protein regions for these amphiphilic and dispersing compounds. Nevertheless, this is a manipulation which is more intricate than that in the case of soluble proteins, specifically on account of the presence of surfactants.

These surfactants must be added at a concentration above their critical micelle concentration (cmc) to all the solutions containing the test protein. In addition to any problems of cost posed by the consumption of surfactants, the experiments are often made difficult due to the fact that the membrane proteins are usually fragile and sensitive to their environment. For example, in the presence of an excess of micelles, they can become denatured, while a surfactant defect generally leads to their precipitation.

Several patents, among which mention may be made of WO-A-9,400,557; WO-A-9,115,505; EP-A-363 106; DE-A-3 527 139; JP-A-6,107,6500; U.S. Pat. No. 5,223,411; JP-A-0,227,0856 and JP-A-0,116,8653 describe the extraction, purification and manipulation of membrane proteins in aqueous medium. These proteins are either dispersed in micellar systems or are inserted into lipid bilayers.

Schafmeister et al. Science, 262, pp. 734–738, 1993 have also described the formation of complexes between membrane proteins and amphiphilic peptide polymers. The amphiphilic polymers concerned are small polypeptides known as peptitergents, which have rigid structures (α-helices), one face of which is hydrophobic and the other face hydrophilic. Peptitergents maintain the solubility of bacteriorhodopsin. However, they are unsuccessful in the case of a porin, no doubt because their rigidity limits their possibilities of adaptation when faced with various hydrophobic surfaces. The authors envisage the use of peptitergents to facilitate the crystallization of membrane proteins.

Mention will also be made, in the field of combinations between amphiphilic synthetic polymers and globular (water-soluble) proteins, of the studies by F. Petit et al. Sci., 273, pp. 777–781, 1995 on modified amphiphilic polyacrylates with a molecular weight of between 150,000 and 200,000. The aim of these investigations relates to the study of protein/polymer combinations (formation of gels, kinetics and energetics of the complexation, in particular) rather than to the maintenance of membrane proteins as disperse solutions.

There is thus a problem to be solved as regards the manipulation of membrane proteins in detergent-free aqueous solutions in the form of dissolved membrane proteins.

The object of the present invention is to solve this problem in general, and the invention in particular proposes novel membrane protein-vinyl polymer of amphiphilic nature complexes which have the following advantages:

production of concentrated solutions of membrane proteins in native form, production of freeze-dried preparations of membrane proteins in native form, low production cost.

The complexes are manipulated in the absence of amphiphilic additives in the medium, which results in a reduction in the purification costs (large volumes of solutions for chromatography, dialyses, etc.).

The term "vinyl" includes acrylic polymers in its general meaning.

The invention thus relates to a membrane protein-vinyl polymer of amphiphilic nature water-soluble complex, characterized in that said vinyl polymer corresponds to the formula:

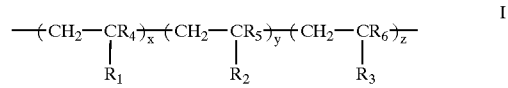

I in which:

$R_1$ is a group:

$COO^- M^+$, $M^+$ being an alkali metal cation, $COOR_7$, $R_7$ being a sugar residue; polyoxyalkylene, in particular polyoxyethylene containing 4 to 10 alkylene oxide units, a radical $(CH_2)_t$—$NR_{10}R_{11}$, t being an integer from 1 to 5, $R_{10}$ and $R_{11}$, which may be identical or different, being a hydrogen atom or a $(C_1$–$C_4)$ alkyl radical, N-pyrrolidonyl, phenyl sulfonate, $CONR_8R_9$, $R_8$ and $R_9$, which may be identical or different, being a hydrogen atom, a sugar residue, polyoxyalkylene, in particular polyoxyethylene containing from 4 to 10 alkylene oxide units, or a zwitterionic radical, $R_4$, $R_5$ and $R_6$, which may be identical or different, are a hydrogen atom or a methyl radical, $R_2$ is a radical $COOR_{12}$ or $CONR_{13}R_{14}$ $R_{12}$ being a linear or branched alkyl or alkenyl radical of 6 to 12 carbon atoms, $R_{13}$ and $R_{14}$, which may be identical or different, have one of the meanings of $R_{12}$, and in addition one of the two can correspond to a hydrogen atom, $R_3$ is a radical $COOR_{15}$ or $CONR_{16}R_{17}$ $R_{15}$ being a $(C_1$–$C_5)$alkyl radical, $R_{16}$ and $R_{17}$ having one of the meanings of $R_{15}$ and in addition it being possible for one of the two to correspond to a hydrogen atom, x, y and z correspond to the respective percentages of the units,
x being between 20 and 90%
y being between 10 and 80%
z being between 0 and 60%,
the average molar mass being between 500 and 100,000, advantageously less than or equal to 50,000, preferably between 1000 and 50,000.

The average molar mass is given by weight.

The polymers which can be used in the context of the present invention are thus amphiphilic polymers which comprise at least one fatty chain, i.e. a hydrophobic portion and hydrophilic units, i.e. a hydrophilic portion.

The meaning of the various substituents indicated in formula I is given in detail below, as a non-limiting guide:

$M^+$ is a lithium, sodium or potassium alkali metal cation, $R_7$ is chosen in particular from:
glucose, fructose, maltose and sucrose residues and in general mono- or disaccharide residues;
H—(OCH$_2$—CH$_2$—)$_{4.8}$; —(CH$_2$)—N—(CH$_2$—CH$_3$)$_2$ $R_8$ and $R_9$ are chosen in particular from glucosamine, fructosamine, maltosamine and saccharosamine residues and in general amino mono- or disaccharide residues;

H—(OCH$_2$—CH$_2$—)$_{4.8}$;

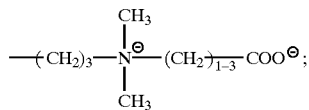

Among the $R_{12}$ to $R_{14}$ alkyl radicals, mention is made in particular of n-hexyl, n-heptyl, n-octyl, n-nonyl, n-decyl, n-undecyl and n-dodecyl radicals, and $C_6$–$C_{12}$ radicals containing a secondary carbon or a tertiary carbon.

Among the $R_{12}$ to $R_{14}$ alkenyl radicals, mention is made in particular of the linear $C_6$–$C_{12}$ radicals mentioned above containing one or two double bonds or the same radicals containing a secondary carbon or a tertiary carbon.

Among the $R_{15}$ to $R_{17}$ alkyl radicals, mention is made in particular of ethyl, isopropyl, n-propyl, n-butyl, isobutyl, sec-butyl, t-butyl, n-pentyl, sec-pentyl, t-pentyl and isopentyl.

Preferably, the invention relates to membrane protein-acrylic polymer of amphiphilic nature water-soluble complexes, characterized in that said acrylic polymers correspond to the formula:

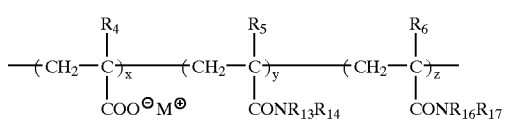

$M^+$, $R_4$, $R_5$, $R_6$, $R_{13}$, $R_{14}$, $R_{16}$, $R_{17}$, x, y and z having the same meaning as in formula I.

The acrylic or vinyl polymers of amphiphilic nature of formula I or II are obtained, in a known manner, from precursor acrylic or vinyl polymers, which may be commercially available or may be synthesized by polymerization of vinyl, acrylic or methacrylic monomers or a mixture of these monomers. In the latter case, copolymers are obtained which, by extension, are included in the general term "polymer". The acrylic polymers of amphiphilic nature of formula II result from the reaction of compounds $R_{13}R_{14}NH$ and optionally $R_{16}R_{17}NH$ with an acrylic polymer, which leads to a random distribution of the amides throughout the chain. The polymer is placed in salified form beforehand or in a subsequent step. Such a mode of synthesis is described, for example, in March, J. (1985) Advanced Organic Chemistry: Reactions, Mechanisms and Structure, pp. 372–374 (Wiley, New York); Wang, T. K., Iliopoulos, I. & Audebert, R. (1988) Polym. Bull 20, 577–582.

Preferred embodiments of the invention, which may or may not be taken in combination with each other or with some of them, are indicated below.

According to a first variant, $R_{13}$ and $R_{14}$ correspond to a hydrogen atom or to a linear alkyl radical of 6 to 12 carbon atoms, it not being possible for $R_{13}$ and $R_{14}$ simultaneously to be a hydrogen atom; $R_{13}$ or $R_{14}$ is preferably an n-octyl radical, the other radical $R_{14}$ or $R_{13}$ being a hydrogen atom.

According to a second variant, $R_{16}$ and $R_{17}$ correspond to an alkyl radical chosen from a group consisting of isopropyl and isobutyl radicals or to a hydrogen atom, it not being possible for $R_{16}$ and $R_{17}$ simultaneously to correspond to a hydrogen atom, According to a third variant:
x is between 30 and 80%
y is between 20 and 70%
z is between 0 and 50%, According to a fourth variant the acrylic polymer of amphiphilic nature is chosen from the group consisting of the polymer in which:
$M^+$ is $Na^+$ or $K^+$
$R_{13}$ is an n-octyl and $R_{14}$ is H
x is between 70 and 80%
y is between 20 and 30%
z is 0%
The average molar mass is between 2000 and 50,000.
$M^+$ is $Na^+$ or $K^+$
$R_{13}$ is an n-octyl and $R_{14}$ is H
$R_{16}$ is an isopropyl and $R_{17}$ is H
x is between 30 and 40%
y is between 20 and 30%
z is between 30 and 50%
The average molar mass is between 2000 and 50,000.

The complex also comprises lipids such as those which come from the migration of the membrane protein during its separation from the detergent molecules.

The complex can comprise any membrane protein of interest as defined in the preamble of the description.

The invention will thus not be limited to a specific category of membrane proteins. However, immunogenic membrane proteins and the membrane proteins of target cells for medicinal products will be mentioned in particular.

Among the membrane proteins, mention is made in particular of the proteins mentioned in Table 4 of Popot and Vitry (Annu. Rev. Biophys. Biophys. Chem. 1990. 19:369–403) pages 375–378, the content of which is incorporated by reference, and the eukaryotic and prokaryotic homologues thereof.

The generality of the mechanism of maintenance in aqueous solution by the polymers is illustrated by the wide diversity of composition and structure of the proteins most extensively studied to date: bacteriorhodopsin is a unique polypeptide with an MM of about 27,000, which is combined with a retinal molecule. The photosynthetic reaction center (MM about 100,000) and cytochrome $b_6f$ (MM about 110,000) are derived from the non-covalent combination of several polypeptides and from other molecules such as hemes, chlorophylls, carotenoids, etc. In addition, $b_6f$ in its native form is a dimer (MM about 220,000). The transmembrane regions of these three proteins consist of bundles of α-helices, whereas porin OmpF (a trimer with an MM of about 111,000) has a β drum structure. As regards the formation of complexes with polymers, no qualitative difference has been detected between these proteins. A modest adjustment of the concentrations of the partners turned out, of course, to be necessary in order to optimize the amount of polymer useful for keeping each protein in solution.

The addition of an amphiphilic polymer of modest molar mass (MM<50,000 g/mol), even at low concentrations, into a dispersion of membrane proteins in micellar medium leads to the formation of a complex. A purification step makes it possible to isolate this complex, which comprises the protein in native form, its possible bound co-factors or lipids and several amphiphilic macromolecules. The behavior of the macromolecules associated with the hydrophobic surfaces of the proteins shows the general characteristics of the adsorption of polymer onto colloids. In particular, the bound polymers no longer dissociate from the complex as long as the solution contains no competing molecules such as surfactants. The protein can then be manipulated like a water-soluble protein, in the absence of free surfactants in the medium.

The amount of acrylic polymer of amphiphilic nature per membrane protein depends, of course, on the size of the polymers and of said proteins. Certain proteins are dimers, trimers or tetramers and will thus be capable of accepting larger or smaller amounts of polymer.

Given these specific details, the complexes according to the invention generally comprise 1 to 100 polymer molecules/protein, advantageously less than 10, it being understood that the number of molecules will depend on the mass of the polymer and on the size of the protein.

The invention also relates to the acrylic polymer of amphiphilic nature/membrane protein complex, in freeze-dried form.

The invention also relates to a highly concentrated aqueous solution of the complex according to the invention, at a concentration advantageously greater than 5 g/l, preferably between 10 and 500 g/l. The membrane proteins in these freeze-dried or highly concentrated forms are in the native state and can thus be readily manipulated and used in various applications.

The invention also relates to a process for preparing the complexes according to the invention, characterized in that a solution of membrane proteins in detergent medium in micellar form is placed in contact with one or more vinyl polymers of amphiphilic nature described above, and in that the concentration of the detergent is lowered to a concentration below the critical micelle concentration and the complex is isolated.

The lowering of the concentration of the detergent can be carried out in a known manner: dilution, adsorption of the detergents, dialysis, separation on molecular sieves or on a gradient, for example.

The formation of detergent micelles/membrane proteins is carried out in a known manner.

The protein-polymer complexes can be separated from the surfactants present in the stock solutions of proteins and of the polymer added in excess by various methods. The adsorption of amphiphilic molecules, on Biobeads SM-2 beads, for example, allows most of the surfactants to be extracted without any consequence on the polymer concentration. By means of dialysis against a buffer solution of pH, the surfactants and polymers not bound to the proteins can be extracted within a few days from the medium containing the complexes. Lastly, it is particularly possible to use sedimentation on a sucrose gradient. Analysis of the sedimentation profiles indicates the absence of aggregates among the protein complexes.

The few residual molecules of surfactant per protein can be compared with the hundreds of bound surfactant molecules per protein in micellar medium. Lipids, which occasionally have a functional role, can remain associated with the complexes. In the soluble complexes obtained, the polymers appear bound to the proteins in proportions which are independent of the initial composition of the protein/surfactant/polymer mixture. However, the mass of polymer bound per protein depends on the type of protein, the pH and the ionic strength.

In general, in order to ensure efficient formation of the complexes, a solution comprising 0.1 to 10 $\mu$M of membrane proteins and 0.005% to 1% of polymer, in grams per gram of solution, is used. This is equivalent to 0.005 g to 1 g of polymer per 100 g of solution.

The addition of the polymers must be carried out before diluting the solution which is at or above the critical micelle concentration.

This complex is reflected in particular by the maintenance of the proteins in soluble form after dilution.

Conservation of the native state is usually essential for applications in biochemistry or in the medical field. The presence has been confirmed in complexes purified by sedimenting all of the subunits constituting complex membrane proteins, such as cytochrome $b_6f$ or the reaction center. The absorption spectra in the visible range for $b_6f$ or for the reaction center do not undergo any change. The spectrum of bacteriorhodopsin, which is very sensitive to the environment of the protein, shows, in the presence of polymer, a shift of a few nanometers toward short wavelengths, similar to that observed in micellar medium. The enzymatic activity of purified complexes of $b_6f$ and of polymers has been measured. When stored in solution, the complexes remain active for several weeks. The rate of degradation is comparable to that of the proteins in standard micellar medium.

The membrane protein-acrylic polymer of amphiphilic nature complexes according to the invention can be used in various applications:

a—simplification of the manipulation of solutions of these proteins, since strict control of the surfactant concentration is no longer necessary.

b—access to protein study techniques which were impossible or difficult to implement in the presence of surfactants or lipid membranes (for example NMR in liquid medium, crystal formation, certain forms of electronmicroscopy, etc.).

c—preparation of concentrated (>10 g/l) and fluid protein solutions.

d—possibility of freeze-drying the preparations in order to store them, and then to resuspend the proteins by simple addition of water or buffer. This opens the way to the commercialization of membrane proteins.

e—novel diagnostic systems using membrane proteins as receptors or as antigens can be envisaged, for example in the search for circulating antibodies which are soluble or borne by lymphocytes: in the first case, the solubility of the membrane protein in the absence of detergent facilitates the development of immunoprecipitation procedures; in the second case, it is possible to present the antigen in soluble form to the cells without risking the cell lysis brought about by the standard surfactants.

f—membrane protein-amphiphilic polymer complexes are potentially of great value in immunology, for the presentation of membrane proteins or other hydrophobic molecules such as immunogens for the purposes of vaccination or the production of antibodies; polymers specially modified to amplify the immune response can be envisaged.

g—many membrane proteins are enzymes, whose complexation with amphiphilic polymers can facilitate their use either industrially or in reagent kits.

h—in pharmacology, the provision of preparations of membrane proteins which are soluble in the absence of surfactant is also capable of allowing the simplification of many tests, for example for measuring the affinity of cell receptors for molecules of pharmaceutical interest.

The invention thus relates to reagent kits comprising, as a guide, at least one complex according to the invention, in particular in the form of a concentrated solution or a freeze-dried preparation.

The invention also relates to diagnostic kits comprising, as a guide, at least one complex according to the invention, in particular in the form of a concentrated solution or a freeze-dried preparation.

Lastly, the invention relates to the novel acrylic polymers of amphiphilic nature of formula II described above, which are useful in particular for the preparation of membrane protein-acrylic polymer of amphiphilic nature complexes.

The examples below illustrate the invention without, however, limiting it:

I—Preparation of the Acrylic Polymers of Amphiphilic Nature

The polymers are prepared by the formation of amide bonds between n-octylamine, optionally isopropylamine and the carboxylic groups of low molecular weight polyacrylic acids:

(molar mass from about 1000 to about 20,000) according to March, J. et al. or Wang, T. K. et al. (op.cit.).

The acrylic polymers of amphiphilic nature obtained are co- or terpolymers randomly grafted along the chain. The polymers obtained are of amphiphilic nature and are not insoluble in water.

The characteristics of some of the polymers obtained are collated in the table below.

The molecular weight is measured using precursor polyacrylates by gel permeation chromatography using polyoxyethylene calibration standards with a narrow MM distribution. MM is the apparent molar mass, in kDa x, y and z are the molar percentages of the non-grafted units of each type, octylamide and isopropylamide, respectively, randomly distributed along the chain.

$$-(CH_2-CH)_{\overline{x}}-(CH_2-CH)_{\overline{y}}-(CH_2-CH)_{\overline{z}}-$$

with side groups: $CO_2^- Na^+$; $CO-NH-CH_2-CH_2-CH_2-CH_2-CH_2-CH_2-CH_2-CH_3$; $CO-NH-CH(CH_3)_2$

| MM | x | y | z |
|---|---|---|---|
| 1 | 3 | 75 | 25 | 0 |
| 2 | 3 | 35 | 25 | 40 |
| 3 | 8 | 75 | 25 | 0 |
| 4 | 8 | 35 | 25 | 40 |
| 5 | 34 | 75 | 25 | 0 |
| 6 | 34 | 35 | 25 | 40 |

The values are indicated under the proviso of the errors intrinsic to the measurements.

II—Preparation of the Membrane Proteins

Bacteriorhodopsin (BR)

The membrane of *Halobacterium salinarium* is dissolved in 100 mM octylthioglucoside (OTG) in 100 mM ammonium phosphate (AP) at pH 8.0 and BR is then purified by centrifugation on a sucrose gradient (5–20% by weight) in the same buffer containing 10 mM OTG (10 h at 54,000 rpm: 250,000×g). The final concentration was 0.1 g/liter in 100 mM AP (pH 8.0), about 10% sucrose, 10 mM OTG.

Cytochrome $b_6f$ from *Chlamydomonas reinhardtii*

The cytochrome $b_6f$ complex from *Chlamydomonas reinhardtii* is purified in the presence of Hecameg® and egg phosphatidylcholine (PC). The final solution contains about 5 μM $b_6f$ complex in 20 mM Hecameg®, 0.1 g/l of PCE and 400 mM NaOH/AP buffer and various protease inhibitors.

Photosynthetic Reaction Center from *Rhodobacter sphaeroides* (RC)

The photosynthetic reaction center from *Rhodobacter sphaeroides* is in a solution at a concentration of about 3 g/l in 20 mM Hecameg®/20 mM NaOH, Tricine, pH 8.0 buffer.

Porin OmpF from *Escherichia coli*

Porin OmpF from *Escherichia coli* is in a solution at a concentration of 4 g/l in 0.2% by weight of octylpolyoxyethylene in the same buffer as above.

III—Preparation of the Complexes

Either 0.05% by weight of polymers or 0.005% is added to a micellar solution of membrane proteins at 0.1 to 5 μM, followed by tenfold dilution with buffer.

After incubation for 15 min at 4° C., the solutions are centrifuged for 30 min at 4° C. at 210,000×g.

The protein concentrations in the supernatant are determined from the absorbance at 564 nm (redox difference spectrum of cytochrome $b_6$); 546 nm (BR); 278 nm (OmpF); 802 nm (RC).

The attached FIG. 1 indicates the weight percentage of membrane proteins in the supernatant with a comparison with:

C1 a dilution in micellar medium,

C2 a dilution with buffer without adding polymer,

C3 a dilution with buffer after adding non-grafted polyacrylate.

The membrane protein used is cytochrome b₆f in black 0.005% polymer in white 0.05% polymer.

Figure 2:
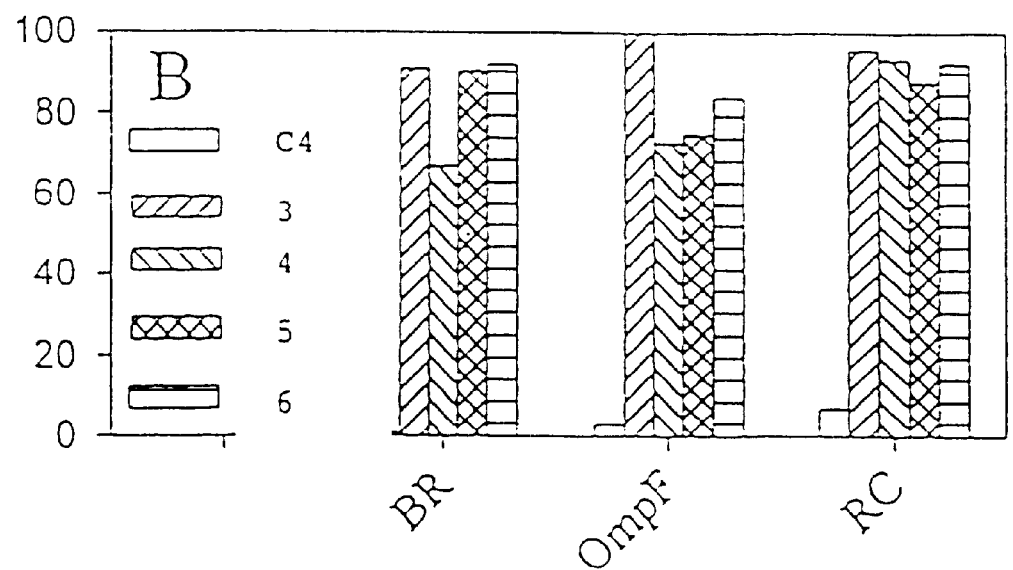

The attached FIG. 2 indicates the weight percentage of membrane proteins in the supernatant (BR, OmpF, RC) in comparison with a buffer medium without polymer (C4).

The tests carried out indicate that these four proteins thus stabilized all have the characteristics of the native proteins.

After dilution in 0.25 mM LM solution, the polymer-cytochrome b₆f complexes catalyzed electron transfers from decylplastoquinol to plastocyanin.

What is claimed is:

1. A membrane protein-vinyl polymer water-soluble complex, comprising a membrane protein and a vinyl polymer which is amphiphilic and has the following formula:

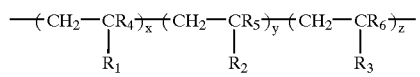

wherein $R_1$ is a group selected from
a) $COO^-M^+$, wherein $M^+$ is an alkali metal cation;
b) $COOR_7$ wherein $R_7$ is selected from a sugar residue, $H-(OCH_2-CH_2-)_{4-10}$, or $(CH_2)_t-NR_{10}R_{11}$, wherein t is an integer from 1 to 5 and $R_{10}$ and $R_{11}$, are the same, or different, and are selected from hydrogen or $(C_1-C_4)$alkyl;
c) N-pyrrolidonyl;
d) phenyl sulfonate; or
e) $CONR_8R_9$, wherein $R_8$ and $R_9$, are the same or different, and are selected from hydrogen atom, a sugar residue, $H-(OCH_2-CH_2-)_{4-10}$, or a zwitterionic radical;

$R_2$ is a group selected from $COOR_{12}$ or $CONR_{13}R_{14}$, wherein $R_{12}$ is a linear or branched alkyl or alkenyl of 6 to 12 carbon atoms, and $R_{13}$ and $R_{14}$, are the same or different, and are selected from a linear or branched alkyl or alkenyl radical of 6 to 12 carbons or one of $R_{13}$ or $R_{14}$ is a hydrogen atom;

$R_3$ is a group selected from $COOR_{15}$ or $CONR_{16}R_{17}$, wherein $R_{15}$ is $(C_1-C_5)$alkyl, and $R_{16}$ and $R_{17}$ are $(C_1-C_5)$alkyl or one of $R_{16}$ or $R_{17}$ is a hydrogen atom;

$R_4$, $R_5$ and $R_6$, are the same or different, and are selected from a hydrogen atom or a methyl radical; x represents the percentage of

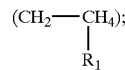

y represents the percentage of

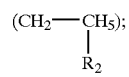

and z represent the percentage of

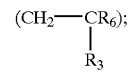

wherein x is between 20–90%, y is between 10–80%, and z is between 0–60%; and the average molar mass is between 500 and 100,000.

2. The membrane according to claim 1 wherein the molar mass is less than or equal to 50,000.

3. The membrane protein-acrylic polymer of amphiphilic nature water-soluble complex according to claim 1, wherein said acrylic polymer is of the formula:

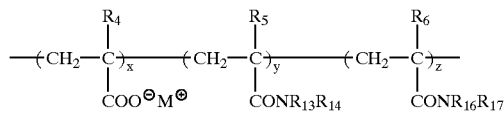

wherein $M^+$, $R_4$, $R_5$, $R_6$, $R_{13}$, $R_{14}$, $R_{16}$, $R_{17}$, x, y and z are as defined in claim 1.

4. The complex according to claim 1 wherein $R_{13}$ is a hydrogen atom or a linear alkyl of 6 to 12 carbon atoms, $R_{14}$ is a hydrogen atom or a linear alkyl of 6 to 12 carbon atoms with the proviso that $R_{13}$ and $R_{14}$ are not both hydrogen atoms.

5. The complex according to claim 4, wherein when one of $R_{13}$ and $R_{14}$ is an n-octyl, the other of $R_{14}$ and $R_{13}$ is a hydrogen atom.

6. The complex according to claim 1, wherein $R_{16}$ is an isopropyl, or isobutyl or a hydrogen atom, $R_{17}$ is an isopropyl, isobutyl or a hydrogen atom with the proviso that both of $R_{16}$ and $R_{17}$ are not hydrogen.

7. The complex according to claim 1 wherein
x is between 30 and 80%,
y is between 20 and 70%, and
z is between 0 to 50%.

8. The complex according to claim 3 wherein:
$M^+$ is $Na^+$ or $K^+$,
$R_{13}$ is n-octyl, $R_{14}$ is hydrogen,
x is between 70 and 80%,
y is between 20 and 30%,
z is 0%, and
the average molar mass is between 2,000 and 50,000.

9. The complex according to claim 3 wherein:
$M^+$ is $Na^+$ or $K^+$,
$R_{13}$ is n-octyl, $R_{14}$ is hydrogen,
$R_{16}$ is isopropyl, $R_{17}$ is hydrogen;
x is between 30 and 40%,
y is between 20 and 30%,
z is between 30 and 50%, and
the average molar mass is between 2,000 and 50,000.

10. The complex according to claim 1 further comprising lipids.

11. The complex according to claim 1 in freeze-dried form.

12. An aqueous solution, comprising the complex according to claim 1 in a concentration of greater than 5 g/l.

13. The solution according to claim 12 wherein the concentration of the complex is between 10 and 500 g/l.

14. A complex according to claim 1, wherein the membrane proteins are selected from the group consisting of eukaryotic and prokaryotic proteins.

15. A process for preparing the complex according to claim 1, comprising the steps of:

preparing a solution of membrane proteins in detergent medium in micellar form, mixing the solution with one or more vinyl polymers of amphiphilic nature according to claim 1, lowering the concentration of detergent to a concentration below the critical micelle concentration and isolating the complex.

16. A kit comprising at least one complex according to claim 15 as a reagent.

17. A diagnostic kit comprising at least one complex according to claim 1 as an immunological reagant.

18. The complex according to claim 14 wherein the protein has enzymatic activity.

* * * * *